(12) United States Patent
Potts et al.

(10) Patent No.: US 10,232,068 B2
(45) Date of Patent: Mar. 19, 2019

(54) PLASMA TREATMENT SYSTEM FOR RIGID CONTAINERS

(71) Applicant: ANACAIL LIMITED, Glasgow (GB)

(72) Inventors: Hugh Potts, Glasgow Lanarkshire (GB); Declan Diver, Glasgow Lanarkshire (GB)

(73) Assignee: Anacail Limited, Glasgow (GB)

( * ) Notice: Subject to any disclaimer, the term of this patent is extended or adjusted under 35 U.S.C. 154(b) by 0 days.

(21) Appl. No.: 15/029,603

(22) PCT Filed: Oct. 15, 2014

(86) PCT No.: PCT/GB2014/053093
§ 371 (c)(1),
(2) Date: Apr. 14, 2016

(87) PCT Pub. No.: WO2015/056006
PCT Pub. Date: Apr. 23, 2015

(65) Prior Publication Data
US 2016/0263262 A1    Sep. 15, 2016

(30) Foreign Application Priority Data
Nov. 5, 2013  (GB) .................................. 1318237.3

(51) Int. Cl.
*A61L 2/14* (2006.01)
*H05H 1/24* (2006.01)

(52) U.S. Cl.
CPC .................. *A61L 2/14* (2013.01); *H05H 1/24* (2013.01); *H05H 1/2406* (2013.01);
(Continued)

(58) Field of Classification Search
CPC ..... A61L 2/00; A61L 2/02; A61L 2/14; H05H 1/00; H05H 1/24
(Continued)

(56) References Cited

U.S. PATENT DOCUMENTS 5,476,634 A * 12/1995 Bridges ..................... A61L 2/04
250/455.11
6,455,014 B1    9/2002 Hammerstrom et al.
(Continued)

FOREIGN PATENT DOCUMENTS

CN         101508338 A     8/2009
EP        2 170 022 A1     3/2010
(Continued)

OTHER PUBLICATIONS

International Search Report and Written Opinion for International Application No. PCT/GB2014/053093, dated Dec. 10, 2014 (11 pages).

(Continued)

*Primary Examiner* — Jason McCormack
(74) *Attorney, Agent, or Firm* — Eric D. Babych; Brinks Gilson & Lione

(57) ABSTRACT

There is herein described a plasma treatment system and a method for sterilizing. More particularly, there is described a plasma treatment system for rigid containers and a method of using the plasma treatment system for sterilizing the rigid containers. In some aspects, the plasma treatment system includes a sterilizing apparatus having a receptacle with a flexible passageway or indentation.

13 Claims, 6 Drawing Sheets

(52) U.S. Cl.
CPC .. *A61L 2202/23* (2013.01); *H05H 2001/2418* (2013.01); *H05H 2001/2425* (2013.01)

(58) Field of Classification Search
USPC ................................ 250/428, 455.11, 453.11
See application file for complete search history.

(56) References Cited

U.S. PATENT DOCUMENTS

| | | | |
|---|---|---|---|
| 2004/0121302 A1* | 6/2004 | Coogan | A61M 1/3681 435/2 |
| 2009/0051272 A1 | 2/2009 | Fukuda et al. | |
| 2011/0300770 A1* | 12/2011 | Fukuda | B32B 15/08 445/58 |
| 2012/0213664 A1* | 8/2012 | Diver | H05H 1/2406 422/22 |

FOREIGN PATENT DOCUMENTS

| | | |
|---|---|---|
| JP | 2008183025 A | 8/2008 |
| WO | WO 2011/055113 A1 | 5/2011 |

OTHER PUBLICATIONS

Communication pursuant to Article 94(3) EPC for related European Application No. 14787031.5, 4 pages (Jan. 26, 2018).
Office Action issued in Chinese application No. 201480056982.4 dated Dec. 28, 2018, 9 pages with translation.

\* cited by examiner

PLASMA TREATMENT SYSTEM FOR RIGID CONTAINERS

CROSS REFERENCE TO RELATED APPLICATIONS

This application is a 371 national phase of International Application No. PCT/GB2014/053093, filed Oct. 15, 2014, and claims the benefit of priority to Great Britain Application No. 1318237.3, filed Oct. 15, 2013, the disclosures of which are incorporated, in their entirety, by this reference.

FIELD OF THE INVENTION

The present invention relates to a plasma treatment system. More particularly, the present invention relates to a plasma treatment system for rigid containers and a method of using said plasma treatment system for sterilising the inside surface and/or contents of said rigid containers.

BACKGROUND OF THE INVENTION

There are many known sterilising techniques but many of these suffer from disadvantages such as poor sterilisation efficiency and the requirement of expensive and complex apparatus.

Initially, we refer to WO 2011/055113 which is incorporated herein by reference. This is a previous application by the present applicant but relates to a system only suitable for flexible packaging.

U.S. Pat. No. 4,834,948 is a conventional coaxial DBD ozone generator. However, the apparatus disclosed therein cannot produce ozone inside a sealed container. The invention disclosed therein is aimed at adding ozone to a flowing gas supplied by a pipe.

JP 2009218083 is a RF powered device operating at very high frequency (MHz-GHz), and again cannot generate ozone inside a pre-sealed container.

EP 1941912 A1 is again a completely different type of device utilising a combination of UV and IR radiation and electron impacts to sterilize objects, rather than chemical agents such as ozone.

US 20110123690 A1 is also a completely unrelated device that simply uses conventional thermal sterilisation on the sealed containers.

U.S. Pat. No. 7,892,611 B2 relates to the area of DBD plasmas but cannot treat a sealed vessel from the outside as an electrode would need to be inserted into the container for it to work.

It is an object of at least one aspect of the present invention to obviate or mitigate at least one or more of the aforementioned problems.

It is a further object of at least one aspect of the present invention to provide an improved sterilisation apparatus for rigid containers.

It is a yet further object of at least one aspect of the present invention to provide an improved method of sterilising rigid containers.

SUMMARY OF THE INVENTION

According to a first aspect of the present invention there is provided a sterilising apparatus comprising:
a receptacle which is capable of being filled with a flexible insulating material or fluid;
located within the receptacle there is a flexible passageway or indentation, the indentation including a fluid deformation of the insulating material conformal with the treatment target container, extending at least partially through the sealed receptacle thereby providing an opening through which a container intended to be sterilised is capable of being inserted and placed;
a series of electrodes located around the flexible passageway or indentation through which a high voltage alternating signal is capable of being applied;
wherein during use the flexible passageway or indentation is capable of being pressed against the container to be sterilised by increasing the pressure in the flexible insulating material or fluid and on application of a high voltage alternating signal to the series of electrodes a plasma is generated within the container to be sterilised.

The present invention therefore relates to sterilising apparatus capable of sterilising the environment in a closed container using a plasma generation technique. The sterilising apparatus may be used in a variety of sterilising situations such as plant material, foodstuff, animal material, medical objects, ophthalmic objects and pharmaceutical or cosmetic products which are located in a sealed container. By sterilisation in the present application also includes decontamination and therefore means reducing the number of viable microrganisms by a factor of, for example, 100 or 100,000.

The plasma will form high energy reactive species inside the container, such as Ozone, Hydroxyl radicals, metastable species and the like. These species can then sterilise all available surfaces on the inside of the sealed container.

Preferably, the container which is to be sterilised is in the form of a rigid container as this allows a tight and close contact to occur between the surface of the flexible passageway or indentation when it is pressurised and forced against the container to be sterilised. The present invention therefore relates to sterilising apparatus capable of treating and sterilising rigid containers made from rigid glass and plastic containers e.g. jars, bottles, drug vials, loaded syringes with air gaps and the like.

The receptacle may be sealed and preferably may be in the form of a sealed box.

The receptacle may be filled with any suitable type of insulating fluid material such as silicone oil or high voltage transformer oil.

The passageway or indentation may extend through substantially the centre of the sealed receptacle from one side to another. The passageway or indentation provides an opening within which containers to be sterilised may be placed.

The passageway or indentation may be made from a flexible material and/or insulating material such as silicone or Viton (registered trade mark). The passageway or indentation may function as an elastic insulating membrane whereupon on placing the insulating fluid under increased pressure the passageway or indentation presses against the container to be sterilised. The insulating fluid surrounds the outside surface of the passageway or indentation. This eliminates any air gap between the elastic insulating membrane forming the passageway or indentation and the container to be sterilised.

Located adjacent and against the material forming the passageway or indentation may be high voltage electrodes which may optionally alternate between positive and negative. The high voltage electrodes may be driven from an electric circuit. The high voltage electrodes may adjust their position as the elastic insulating membrane forming the passageway or indentation expands and contracts.

Connected to the receptacle there may be a device which can be used to increase the pressure of the insulating liquid"

material contained in the receptacle. In a particular embodiment, a piston in for example the form of a syringe may be used to compress the insulating liquid material thereby forcing the flexible material forming the passageway or indentation onto the container to be sterilised.

During operation the container to be treated is placed in the flexible passageway or indentation. The pressure in the insulating fluid material is then increased which has the result that the flexible passageway or indentation is pressed hard against the container, with the electrodes staying in contact with the container. This will apply an even pressure (approx. 0.1-1 Bar) to the outside of the container, which will exclude all air between the flexible membrane of the passageway or indentation and the surface of the container to be sterilised.

A high voltage alternating signal (~5-20 kVrms, 1-50 kHz) may be applied to the electrodes which will break down the gas in the sealed container forming a plasma against its walls. The plasma will generate chemically active species such as oxygen or hydroxyl radicals, ozone, nitrogen metastables inside the sealed container. These species can have a variety of effects, from decontaminating or sterilising the bottle or jar contents or inside surfaces and destroying unwanted organic solvents.

According to a second aspect of the present invention there is provided a method of sterilising apparatus comprising:

a receptacle which is capable of being filled with a flexible insulating material or fluid;

located within the receptacle there is a flexible passageway or indentation, the indentation including a fluid deformation of the insulating material conformal with the treatment target container, extending at least partially through the sealed receptacle thereby providing an opening through which a container intended to be sterilised is capable of being inserted and placed;

a series of electrodes located around the flexible passageway or indentation through which a high voltage alternating signal is capable of being applied;

wherein during use the flexible passageway or indentation is capable of being pressed against the container to be sterilised by increasing the pressure in the flexible insulating material or fluid and on application of a high voltage alternating signal to the series of electrodes a plasma is generated within the container to be sterilised.

The sterilising apparatus may be as defined in the first aspect.

According to a third aspect of the present invention there is provided a sterilising apparatus comprising:

a receptacle which is capable of being filled with a flexible insulating material or fluid;

locating within the receptacle a flexible passageway extending at least partially through the sealed receptacle thereby providing an opening through which a container intended to be sterilised is capable of being inserted and placed where the container is at least partially filled with a conductive material, two electrodes around the flexible passageway across which a high voltage alternating signal is capable of being applied and the lower electrode wraps entirely around the passageway, and hence around any container inserted into the passageway;

wherein during use the flexible passageway is capable of being pressed against the container to be sterilised by increasing the pressure in the flexible insulating material or fluid.

On application of a high voltage alternating signal to the pair of electrodes, the large area between the lower electrode and the conductive jar contents results in efficient capacitive coupling between the jar contents and the lower electrode. Almost the entire driving alternating voltage will then appear between the conductive jar contents and the upper electrode generating a plasma inside the container between the conductive container contents and the container wall This system is therefore limited to containers filled with conductive liquids, such as most foods and aqueous solutions, but not dry materials or oils. It is particularly suitable where there is very little headspace in the jar, as a much higher power density can be safely obtained at a lower operating voltage.

The conductive material may for example be a wet food or drink, or an aqueous solution.

BRIEF DESCRIPTION OF THE DRAWINGS

Embodiments of the present invention will now be described, by way of example only, with the reference to the accompanying drawings in which:

FIG. 6b shown the electrics operating the sterilisation apparatus shown in FIG. 6a.

BRIEF DESCRIPTION

Generally speaking the present invention resides in the provision of an apparatus capable of providing an electrical discharge (i.e. plasma) inside a sealed, rigid container such as a bottle or jar. The plasma will form high energy reactive species inside the container, such as Ozone, Hydroxyl radicals, metastable species and the like. These species can then sterilise or decontaminate all surfaces, and the gas volume within the sealed container.

The present invention relates to sterilising apparatus capable of treating and sterilising rigid containers made from rigid glass and plastic containers e.g. such as jars, bottles, drug vials, loaded syringes with air gaps and the like.

Figure 1:
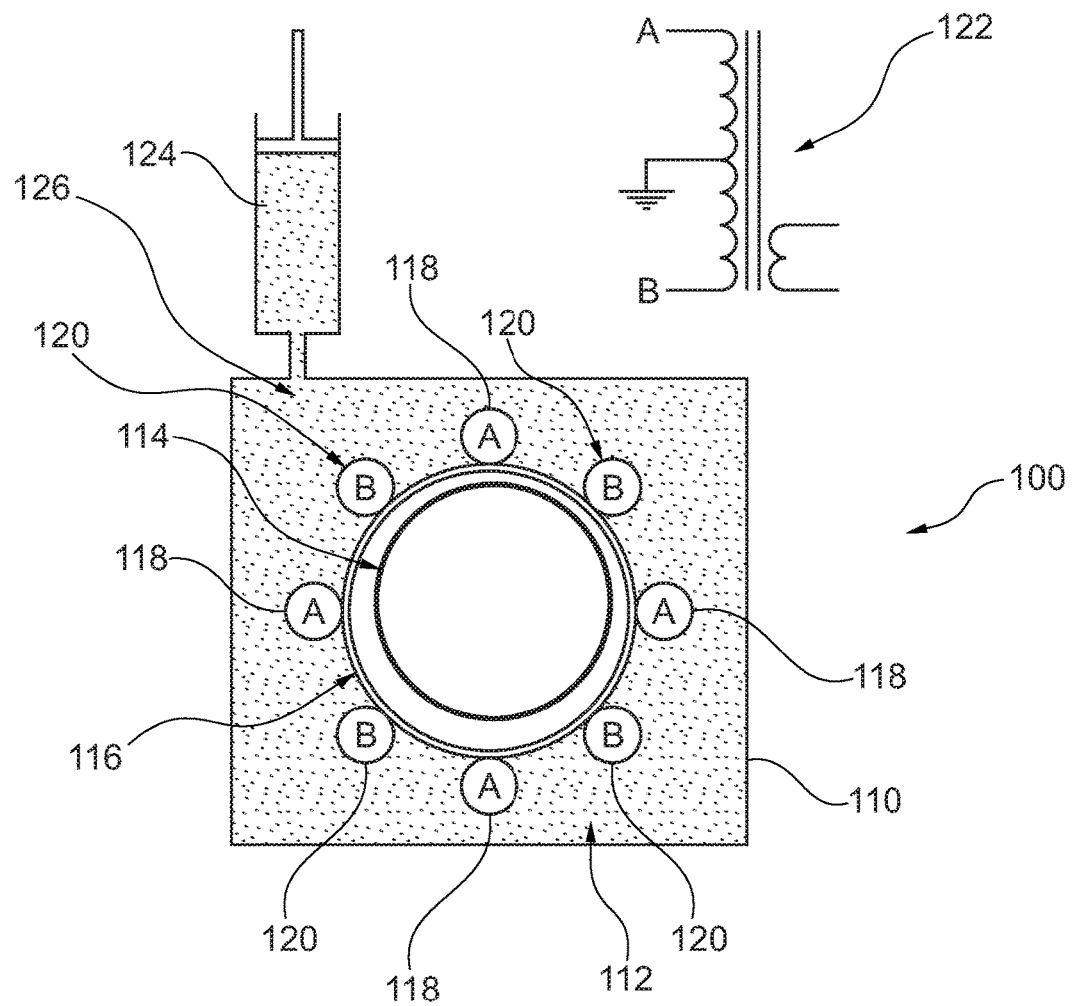
FIG. 1 is a representation of sterilisation apparatus according to an embodiment of the present invention where there is reduced pressure in a fluid surrounding a container to be treated.
Figure 2:
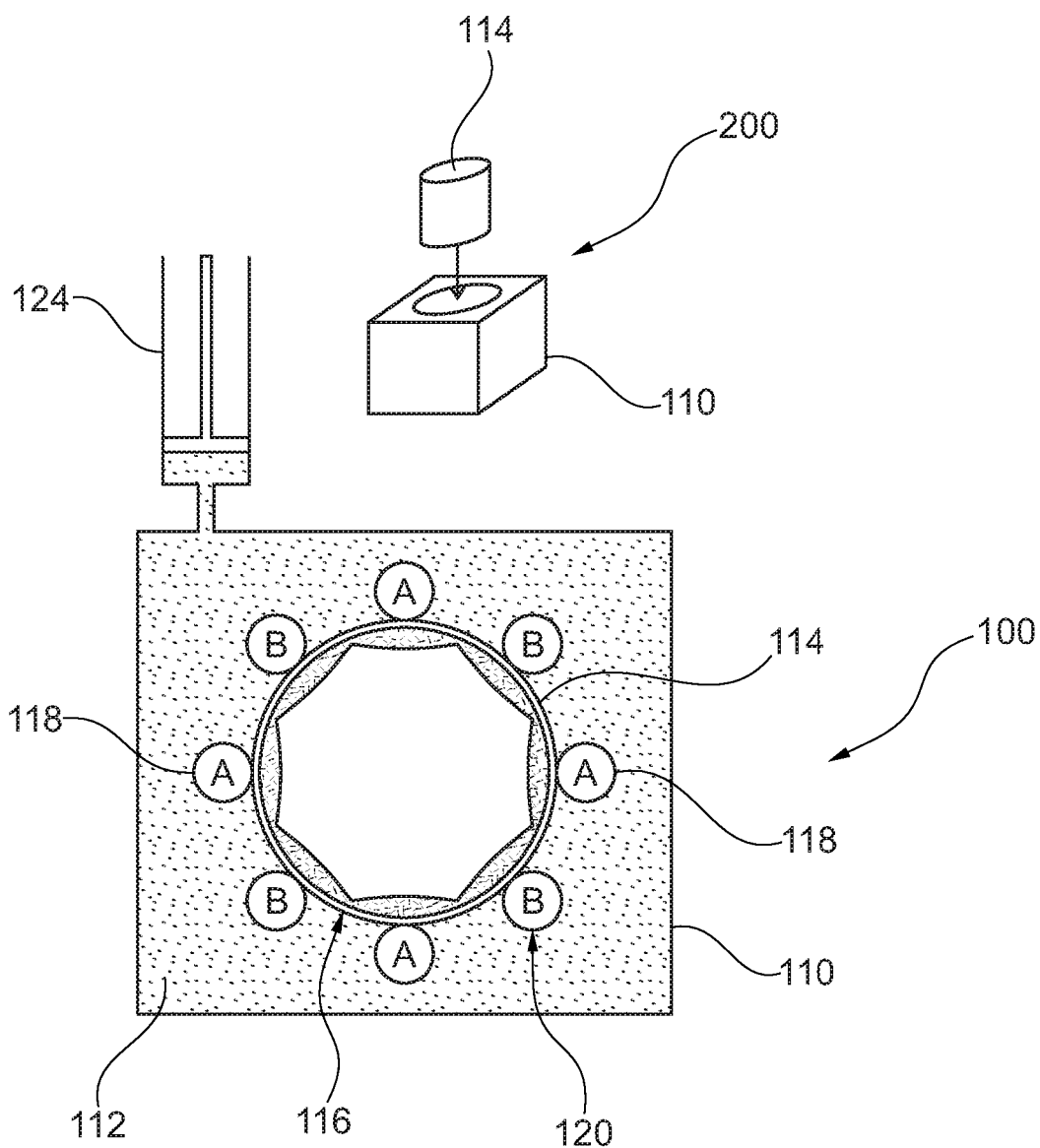
FIG. 2 is further representation of the apparatus shown in FIG. 1 where the fluid surrounding the container is pressurised.

FIG. 1 is a representation of a sterilising apparatus according to the present invention generally designated 100. There is shown a sealed box 110 which is filled with an insulating fluid material 112 e.g. silicone oil or high voltage transformer oil. Located within the sealed box 110 there is a container 114 which is to be sterilised. FIG. 1 shows that there is a passageway 116 extending through substantially the centre of the sealed box 110. The passageway 116 provides an opening within which containers 114 to be sterilised may be placed.

The passageway 116 is made from a flexible material and/or insulating material such as silicone or Viton (registered trade mark). The passageway 116 therefore functions as an elastic insulating membrane. Located adjacent and against the material forming the passageway 116 are high voltage electrodes which are positive 118 and negative 120. The high voltage electrodes 118, 120 are driven from an electric circuit generally designated 122.

FIG. 1 also shows that there is a piston and cylinder assembly 124. In FIG. 1 the piston 124 is in an extended configuration and has the effect of reducing pressure in the fluid 112 at the opening 126 into the sealed box 110. Pressed against the flexible passageway 116 are the high voltage electrodes 118, 120, which are pressed outwards by atmospheric pressure when the pressure in the insulating fluid 112 is reduced by means of the piston 124.

During operation the container 114 to be treated is placed in the flexible passageway 116 as shown by representation 200. The piston 124 is then depressed which has the result that the flexible passageway 116 is pressed hard against the container 114, with the electrodes 118,120 staying in contact with the container 114. The pressure in the insulating fluid material 112 is therefore increased. This will apply an even pressure (approx. 0.1-1 Bar) to the outside of the container 114, which will exclude all air between the flexible membrane of the passageway 116 and the surface of the container 114 to be sterilised.

A high voltage alternating signal (~5-20 kVrms, 1-50 kHz) is applied to the electrodes 118,120 as shown, which will break down the gas in the sealed container 114 forming a plasma against its walls. The plasma will generate chemically active species such as oxygen or hydroxyl radicals, ozone, nitrogen metastables inside the sealed container 114. These species can have a variety of effects, from decontaminating or sterilising the bottle or jar contents or inside surfaces, destroying unwanted organic solvents. This signal driving this plasma can be modulated in amplitude and duty cycle to achieve the required chemistry.

After the inside of the sealed container 114 has been treated and sterilised with plasma the pressure in the fluid 112 is then released by allowing the piston 124 to return to its original position shown in FIG. 1.

The container 114 which is now sterilised can now be removed, now containing active species which continue to sterilise its inside surfaces. Over time (minutes to hours depending on the temperature and container contents) these species will decay, leaving the container 114 sterilised, and no toxic residues.

In the case where the container 114 contains an aqueous solution, the ozone formed inside the container 114 will readily dissolve into solution, and can thus sterilise the liquid. The speed that the ozone dissolves into solution can be increased by agitating the container, or coupling ultrasound into it.

Figure 3:
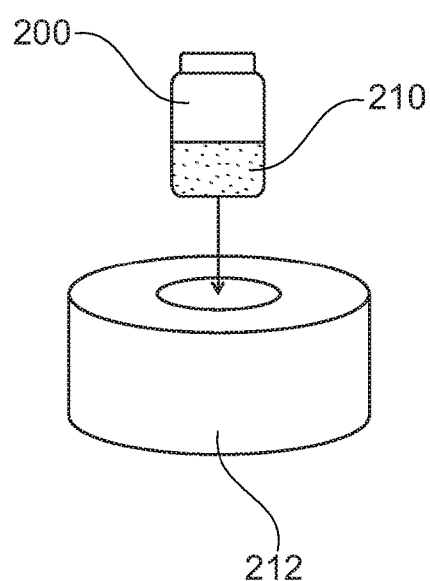
FIG. 3 is a view of sterilisation apparatus according to a further embodiment of the present invention.
Figure 3:
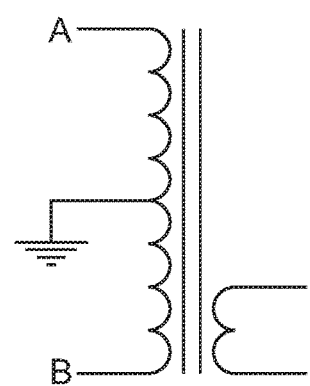

FIG. 3 represents a further embodiment where there is an annular device 200 which is in the form of a cylindrical tube with thick walls made from an insulating, resilient material such as silicone rubber. A fluid 210 is inside the container 200. In FIG. 3 a container 200 filled with material is ready to be inserted into the hole in the annular device 200.

Figure 4:
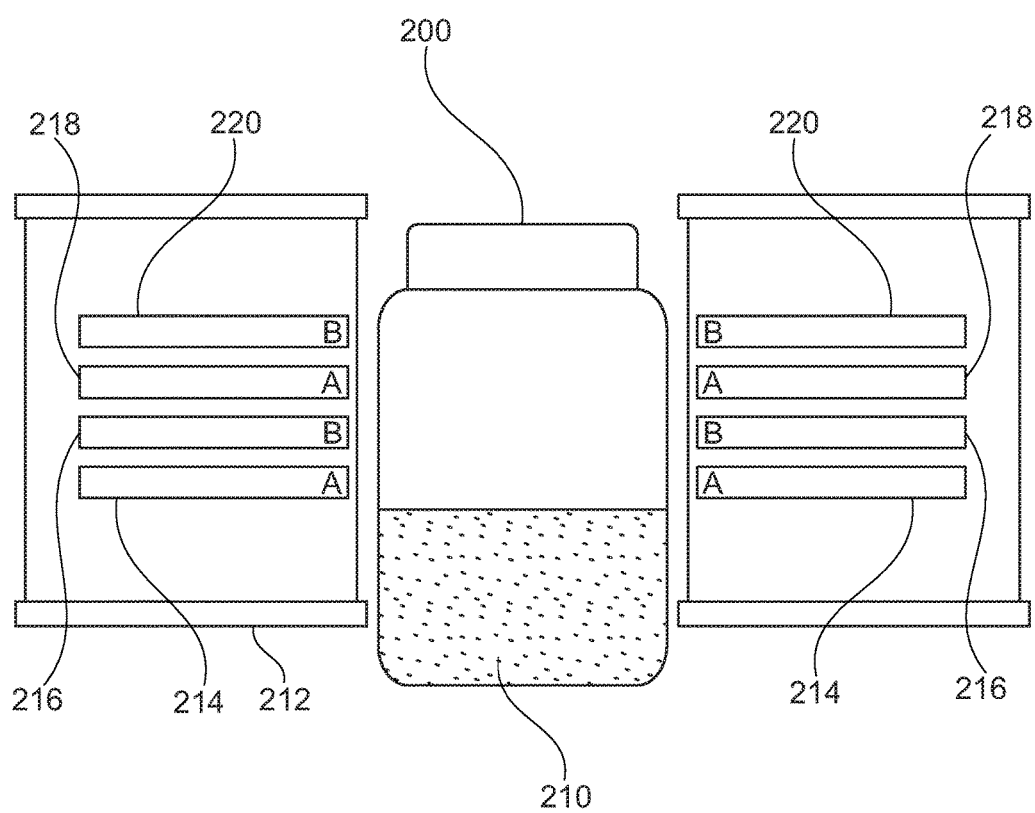
FIG. 4 is a further representation of the apparatus shown in FIG. 3 wherein a container is being placed in the sterilisation apparatus.
Figure 5:
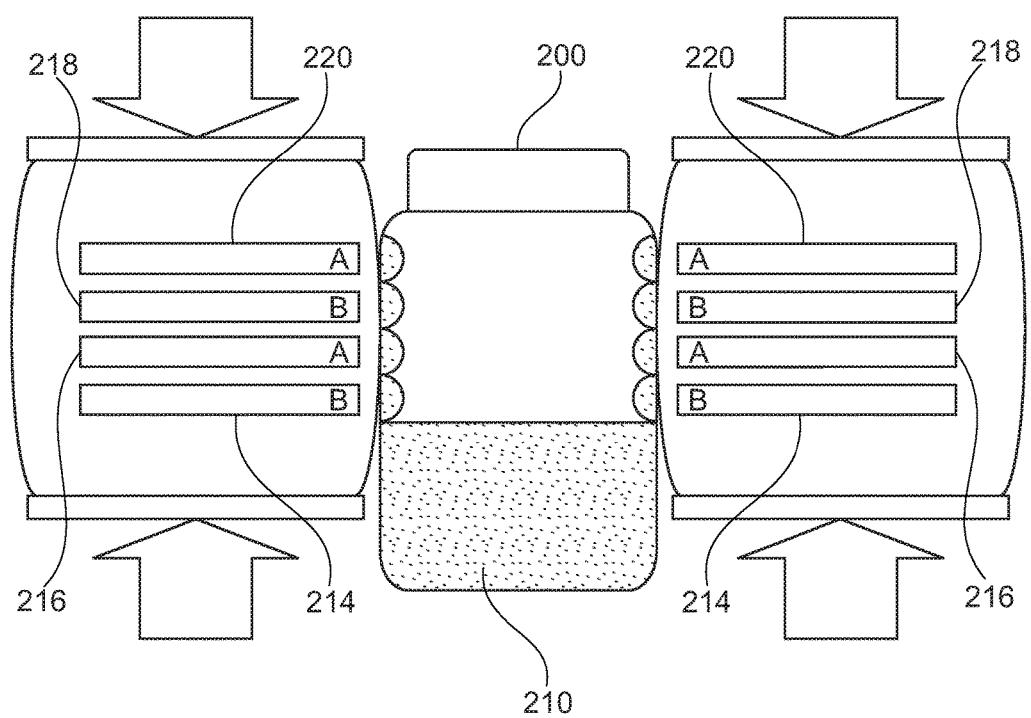
FIG. 5 is a view of the sterilisation apparatus shown in FIGS. 3 and 4 in use.

The walls of the annular device as shown in FIGS. 4 and 5 have multiple flexible conductive electrodes 214,216,218, 220 moulded into them. Each electrode 214,216,218,220 has the shape of a circle with a hole through the middle.

The flexible electrodes 214,216,218,220 are made from a conductive version of the same resilient material as the tube, and are fully encapsulated by the tube insulating material. Alternate electrodes are connected to an alternating high voltage source (5-20 kVrms, 1-50 kHz, pulse shaping).

As shown in FIG. 5 in operation the container 210 to be treated is placed into the hole in the centre of the annular device 200. Pressure is applied to the top surface of the tube, compressing it vertically, causing it to expand horizontally, gripping the container 200. The resilient tube is designed such that all air between the bore of the tube and the vessel is expelled (there mat optionally be a confining ring or tube on the outside). A high voltage, high frequency signal is then applied to the electrodes 214,216,218,220, breaking down the air inside the container 200 as before. The present invention therefore relates to a system for generating an electrical discharge inside a rigid, insulating container using wholly external electrodes. A rigid container can be placed inside the system, such that electrodes are in close proximity to the walls of vessel. An insulating material fully fills all gaps between electrodes and the vessel, and all gaps between electrodes.

A high alternating voltage (sinusoidal or shaped pulse) is applied to alternate electrodes, generating an intense electric field. Where this electric field meets gas inside the vessel an electrical discharge or plasma forms generating ozone and other active species.

Figure 6A:
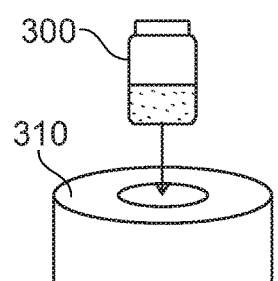
FIG. 6a is a representation of a further embodiment of the present invention showing a sterilisation apparatus where a filled container is being placed into the sterilisation apparatus.
Figure 6B:
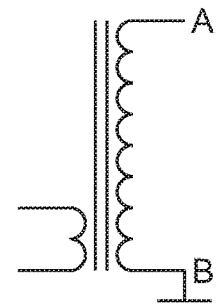
Figure 6C:
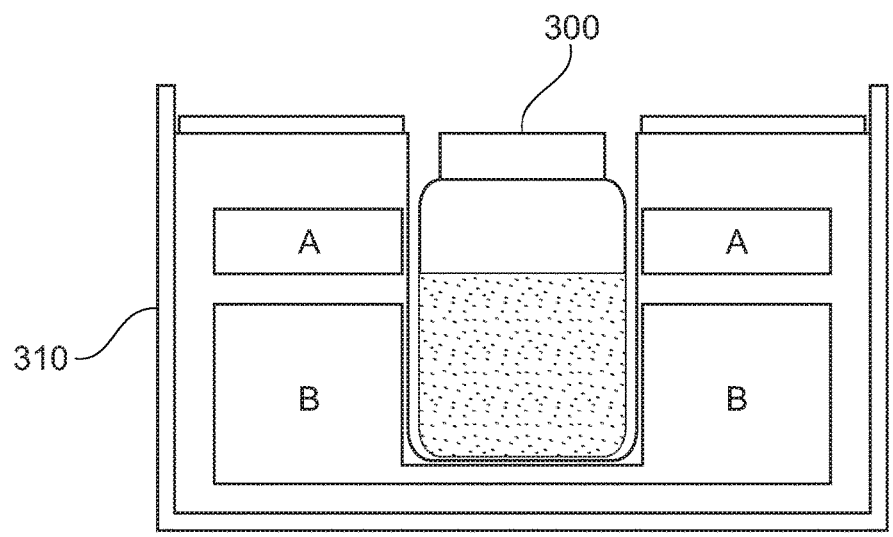
FIGS. 6c and 6d shows the filled container shown in FIG. 6a placed in the sterilisation apparatus with the container contents capacitatively coupled to the high voltage supply in FIG. 6d.
Figure 6D:
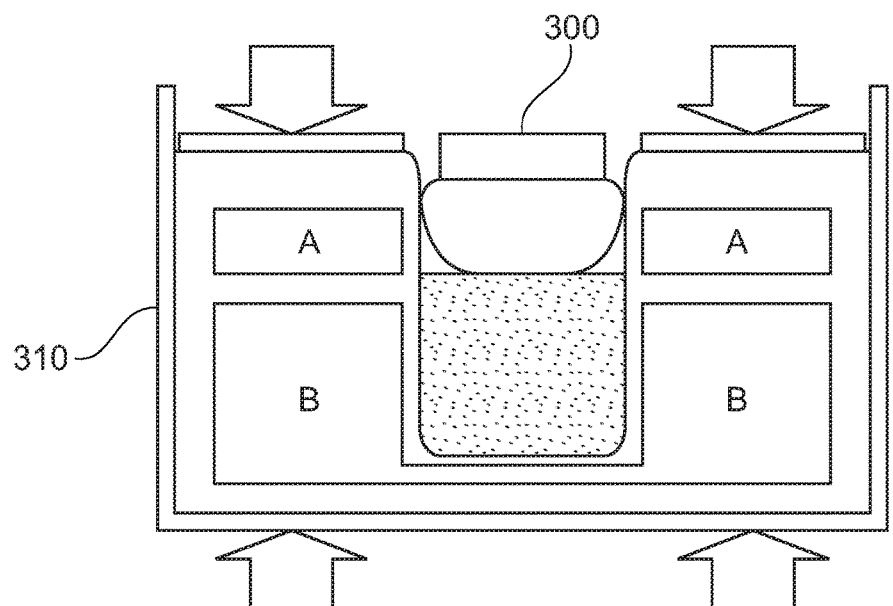

In FIG. 6a there is a shown a filled container 300 being placed in a sterilisation apparatus 310. In FIG. 6c the electrodes are formed from a flexible elastomeric material. A liquid insulator system (like that in FIG. 1 in the patent) would work just as well.

The rigid container 300 is placed into the passage or indentation, and pressure applied to the top of the elastomeric material as before. This causes all air to be expelled around the jar as the elastomer conforms to the container outer surface. High voltage, high frequency power (3-15 kVrms, 1-50 kHz) is applied between electrodes A and B. B may be optionally grounded, but may be powered with an opposite phase to A. Due to the relatively large capacitance between electrode B and the container contents the container contents becomes closely electrically coupled to B, with only a small voltage drop across the jar wall. A very large electric field is therefore present between electrode A and the jar contents, causing the gas in the jar to form a plasma. This system has the advantage that it can operate at lower driving voltages than the systems in FIGS. 1-5.

If the jar is very full, then electrode A can be omitted from the elastomer, and an electrode in contact with the lid, or the lid itself (if conductive) can be used. In this case for safety reasons electrode A would probably be grounded, and electrode B powered.

The apparatus of the present invention may be used in a variety of sterilising situations:
1) Medical
    Endpoint sterilisation of thermally sensitive drugs (particularly radioactive drugs such as PET tracers) where there is not time for conventional validation (culture) of sterility due to the short half-life of the radioactive element;
2) Industrial
    Sterilisation of bottles and jars prior to filling—relevant in the food, drink and cosmetics industries; and 3) Food
    Sterilisation or decontamination of the top exposed food surface of sealed bottles and jars.

Whilst specific embodiments of the present invention have been described above, it will be appreciated that departures from the described embodiments may still fall within the scope of the present invention. For example, any suitable type of shape and type of flexible passageway may be used which may be pressed against a rigid container to be sterilised. Moreover, any type of plasma generation may be used. The apparatus of the present invention may also be used in any type of situation where sterilisation is required.

The invention claimed is:

1. A sterilizing apparatus comprising:
   a receptacle to form a sealed receptacle which is filled with a flexible insulating material or fluid;
   located within the receptacle there is a flexible passageway or indentation, the indentation including a fluid deformation of the insulating material conformal with a treatment target container, extending at least partially through the sealed receptacle thereby providing an opening through which a container intended to be sterilized is capable of being inserted and placed;
   a series of electrodes located around the flexible passageway or indentation through which a high voltage alternating signal is capable of being applied;
   wherein connected to the sealed receptacle there is a device which can be used to increase pressure of the flexible insulating material or the fluid contained in the sealed receptacle;
   wherein during use the device applies the pressure to an outer surface of the receptacle, thereby compressing the flexible insulating material or the fluid and causing the receptacle to expand such that the flexible passageway or indentation presses against the container to be sterilized and on application of the high voltage alternating signal to the series of electrodes a plasma is generated within the container to be sterilized.

2. A sterilizing apparatus according to claim 1, wherein the plasma formed will form high energy reactive species inside the container including Ozone, Hydroxyl radicals and metastable species which are used to sterilize all available surfaces and gas contained on the inside of the container.

3. A sterilizing apparatus according to claim 1, wherein the container is in the form of a rigid container as this allows a tight and close contact to occur between the surface of the flexible passageway or indentation when it is pressurized and forced against the container.

4. A sterilizing apparatus according to claim 1, wherein the container is rigid, sealed and made from rigid glass or plastic.

5. A sterilizing apparatus according to claim 1, wherein the receptacle is in the form of a sealed box.

6. A sterilizing apparatus according to claim 1, wherein the receptacle is filled with insulating fluid material selected from silicone oil and high voltage transformer oil.

7. A sterilizing apparatus according to claim 1, wherein the passageway or indentation extends through substantially the center of the sealed receptacle from one side to another.

8. A sterilizing apparatus according to claim 1, wherein the passageway or indentation is made from a flexible material and/or insulating material.

9. A sterilizing apparatus according to claim 1, wherein the passageway or indentation functions as an elastic insulating membrane whereupon on placing the insulating fluid under increased pressure the passageway or indentation presses against the container to be sterilized which eliminates any air gap between the elastic insulating membrane forming the passageway or indentation and the container to be sterilized.

10. A sterilizing apparatus according to claim 1, wherein located adjacent and against the material forming the passageway or indentation there are high voltage electrodes.

11. A sterilizing apparatus according to claim 10, wherein the high voltage electrodes are driven from an electric circuit and are capable of adjusting their position as an elastic insulating membrane forming the passageway or indentation expands and contracts.

12. A sterilizing apparatus according to claim 1, wherein the device is a piston and is used to compress an insulating liquid material thereby forcing the flexible insulating material forming the passageway or indentation onto the container to be sterilized.

13. A method of using the apparatus of claim 1, comprising:
    pressing the flexible passageway or indentation against the container to be sterilized; increasing the pressure in the flexible insulating material or fluid; applying a high voltage alternating signal to the series of electrodes; and generating the plasma within the container to be sterilized.

* * * * *